US008895029B2

United States Patent
Rinehart

(10) Patent No.: US 8,895,029 B2
(45) Date of Patent: Nov. 25, 2014

(54) COMPOSITIONS AND METHODS FOR VACCINATING CATTLE

(71) Applicant: Carol L. Rinehart, Parkville, MO (US)

(72) Inventor: Carol L. Rinehart, Parkville, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 14/153,153

(22) Filed: Jan. 13, 2014

(65) Prior Publication Data

US 2014/0127259 A1      May 8, 2014

Related U.S. Application Data

(62) Division of application No. 13/310,915, filed on Dec. 5, 2011, now abandoned.

(60) Provisional application No. 61/421,622, filed on Dec. 9, 2010.

(51) Int. Cl.
| | | |
|---|---|---|
| *A61K 39/02* | (2006.01) | |
| *A01N 63/00* | (2006.01) | |
| *A61K 39/00* | (2006.01) | |
| *A61K 49/00* | (2006.01) | |
| *A61K 39/12* | (2006.01) | |
| *A61K 39/295* | (2006.01) | |

(52) U.S. Cl.
CPC .............. *A61K 39/295* (2013.01); *A61K 39/12* (2013.01); *A61K 2039/70* (2013.01); *A61K 39/02* (2013.01); *A61K 2039/521* (2013.01); *A61K 39/0225* (2013.01); *A61K 2039/552* (2013.01); *A61K 2039/5254* (2013.01); *C12N 2770/24334* (2013.01); *C12N 2760/18634* (2013.01); *C12N 2760/18534* (2013.01); *C12N 2710/16734* (2013.01); *Y10S 424/823* (2013.01); *Y10S 424/813* (2013.01)
USPC .................... 424/234.1; 424/184.1; 424/823; 424/813; 424/93.4; 424/9.2

(58) Field of Classification Search
None
See application file for complete search history.

(56) References Cited

U.S. PATENT DOCUMENTS

2009/0068223 A1    3/2009   Meyers et al.

OTHER PUBLICATIONS

Boehringer Ingelheim Vetmedica, Inc. "BVD Overview: The Economic Drain Caused by BVD Starts with the Cow/Calf Herd". 2008, 6 pages.
Boehringer Ingelheim Vetmedica, Inc. "BVD Overview: The Economic Drain Caused by BVD Starts with the Dairy Cow Herd". 2008, 6 pages.
Boehringer Ingelheim Vetmedica, Inc., "Material Safety Data Sheet Express FP 3-VL5". Jun. 5, 2007, Retrieved from the Internet: URL: http://www.bi-vetmedica.com/content/dam/internet/ah/vetmedica/com_EN/MSDS/Express_FP3VL5_msds.pdf [Retrieved on Mar. 7, 2012], 10 pages.
Boehringer Ingelheim Vetmedica, Inc., "Technical Bulletin: Safety of Express® MLV vaccines in pregnant cows or calves nursing pregnant cows". 2008, 4 pages.
Bolin et al., "Effect of vaccination with a pentavalent leptospiral vaccine containing *Leptospira interrogans* serovar hardjo type hardjo-bovis on type hardjo-bovis infection of cattle". American Journal of Veterinary Research, vol. 50, No. 12, Dec. 1989, pp. 2004-2008.
Bolin et al., "Use of a monovalent leptospiral vaccine to prevent renal colonization and urinary shedding in cattle exposed to *Leptospira borgpetersenii* serovar hardjo ". American Journal of Veterinary Research, vol. 62, No. 7, Jul. 2001, pp. 995-1000.
Brown et al., "Comparison of three different leptospiral vaccines for induction of a type 1 immune response to *Leptospira borgpetersenii* serovar Hardjo ". Vaccine, vol. 21, Nos. 27-28, Oct. 2003, pp. 4448-4458.
International Search Report and Written Opinion for PCT/US2011/063219 mailed on Mar. 21, 2012.
Intervet. "Efficacy of VL5 SQ (*Campylobacter fetus*-Leptospira Canicola-Grippotyphosa-Hardjo-Icterohaemorrhagiae-Pomona) Multivalent Bacterin". 2005, 6 pages.

*Primary Examiner* — S. Devi
(74) *Attorney, Agent, or Firm* — Michael P. Morris; Wendy M. Gombert

(57) ABSTRACT

The present invention relates to compositions, uses thereof, and methods of vaccinating cattle, particularly cows and heifers, against *Leptospira borgpetersenii* serovar *hardjo* (type *hardjo-bovis*) by using *Leptospira interrogans* serovar *hardjo* (type *hardjoprajitno*).

5 Claims, No Drawings

COMPOSITIONS AND METHODS FOR VACCINATING CATTLE

BACKGROUND OF THE INVENTION

A. Field of the Invention

The present invention relates to compositions, uses thereof, and methods of vaccinating cattle, particularly cows and heifers, against *Leptospira borgpetersenii* serovar *hardjo* (type *hardjo-bovis*) by using *Leptospira interrogans* serovar *hardjo* (type *hardjoprajitno*).

B. Description of the Related Art

Leptospirosis is the most widespread zoonotic disease in the world. It affects most mammals and is an important cause of reproductive failure in cattle throughout the world. (See Faine et al., 1999; Heath and Johnson, 1994.) Leptospires are gram-negative, thin, helical bacteria classified into at least twelve pathogenic and four saprophytic species, with more than 250 pathogenic serovars. The bacteria may survive in the environment for up to six months, preferably in basic soils (pH of 7.2 to 8.0) and in a warm, moist environment. The bacteria rarely survive in dry or extreme cold conditions. (See Faine et al., 1999; Heath and Johnson, 1994.)

Pathogenic species persist as chronic infections of the renal tubules of the maintenance host, sometimes causing very little or no disease. Transmission occurs through direct contact with infected urine or by contact through feed or bedding contaminated with infected urine. In cattle, common clinical signs of the disease include reproductive failure, weak calves, abortion, stillbirths, mummification, and agalactia. Shedding of the bacteria in urine may occur for extended lengths of time. Renal lesions may be the direct result of leptospiremia from infection with *Leptospira* serovars *hardjo, pomona*, and *grippotyphosa*. (See Faine et al., 1999; Heath and Johnson, 1994; Ellis, 1994.)

Cattle are the primary maintenance host reservoir for *Leptospira interogans* serovar *hardjo* (type *hardjoprajitno*) (LHP) and *Leptospira borgpetersenii* serovar *hardjo* (type *hardjo-bovis*) (LHB). LHP is found primarily in Europe, whereas the most common cause of leptospirosis in cattle throughout much of the world is LHB. LHB is the only *hardjo* serovar that has been isolated to date from cattle in the United States. (Bolin, et. al., 1989(a).)

Vaccination with whole cell inactivated leptospiral vaccine containing *Leptospira* serovars *hardjo, canicola, pomona, grippotyphosa*, and *icterohaemorrhagiae* is the primary means of controlling leptospirosis in cattle. Because the costs associated with the manufacture of a vaccine are directly related to the type(s) and number of components used to formulate the vaccine, it is desirable to reduce the number of components in the vaccine without loss of vaccine effectiveness. Herein, are described vaccines, as well as associated methods and uses that provide protection against *Leptospira borgpetersenii* serovar *hardjo* (type *hardjo-bovis*) without including the serovar *hardjo* (type *hardjo-bovis*) in the vaccines.

SUMMARY OF THE INVENTION

The present invention provides immunogenic compositions, vaccines, and related methods and uses that overcome deficiencies in the art. The compositions, methods, and uses provide protection against, reduction in the incidence, and/or lessen the severity of infection by *Leptospira borgpetersenii* serovar *hardjo* (type *hardjo-bovis*) by vaccinating with *Leptospira interrogans* serovar *hardjo* (type *hardjoprajitno*).

Immunogenic compositions and vaccines of the invention comprise a *Leptospira interrogans* serovar *hardjo* (type *hardjoprajitno*) bacterium or bacteria capable of provoking an immune response against *Leptospira borgpetersenii* serovar *hardjo* (type *hardjo-bovis*). Preferably, the *Leptospira interrogans* serovar *hardjo* (type *hardjoprajitno*) is a killed bacterium or bacteria.

Immunogenic compositions and vaccines of the invention can further comprise one or more modified live viruses (MLVs) selected from the group consisting of Infectious Bovine Rhinotracheitis (IBR) virus, Bovine Virus Diarrhea (BVD) Types 1 and 2, Parainfluenza 3 (PI3) virus, and Bovine Respiratory Syncytial Virus (BRSV). Preferred immunogenic compositions and vaccines include a combination of killed *Leptospira interrogans* serovar *hardjo* (type *hardjoprajitno*), modified live Infectious Bovine Rhinotracheitis (IBR) virus, modified live Bovine Virus Diarrhea (BVD) Type 1 and modified live BVD Type 2—such as the licensed commercially available combination product, EXPRESS FP® 5 VL5, Boehringer Ingelheim Vetmedica, Inc., St. Joseph. Immunogenic compositions and vaccines of the invention may also comprise modified live Bovine Respiratory Syncytial Virus (BRSV), or a combination of killed *Campylobacter* Fetus, *Haemophilus somnus*, and any of *Leptospira* serovars *canicola, grippotyphosa, hardjo, icterohaemorrhagiae*, and *pomona*.

Immunogenic compositions and vaccines of the invention provide protection against, reduction in the incidence, and/or lessen the severity of infection by *Leptospira borgpetersenii* serovar *hardjo* type *hardjo-bovis* in a subject. Preferably, the subject is a bovine, more preferably the bovine is a cow or heifer, most preferably the bovine is a heifer.

Immunogenic compositions of the invention which comprise at least one or more *Leptospira interrogans* serovar *hardjo* type *hardjoprajitno* bacterium or bacteria as defined herein may further comprise a physiologically-acceptable vehicle such as a pharmaceutically or veterinarily acceptable carrier, adjuvant, or combination thereof.

Any of the *Leptospira interrogans* serovar *hardjo* type *hardjoprajitno* bacteria provided herewith or any immunogenic compositions comprising one or more *Leptospira interrogans* serovar *hardjo* type *hardjoprajitno* bacterium or bacteria provided herewith can be used as a medicament, preferably as a vaccine or immunogenic composition, most preferably for the prophylaxis or treatment of a subject against a *Leptospira borgpetersenii* serovar *hardjo* type *hardjo-bovis* infection.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

The invention also provides methods, as well as uses of the compositions of the invention, for providing protection against, reduction in the incidence, and/or lessening the severity of infection by *Leptospira borgpetersenii* serovar *hardjo* type *hardjo-bovis* in a subject comprising administering to the subject an immunogenic composition or vaccine, wherein the immunogenic composition or vaccine includes a *Leptospira interrogans* serovar *hardjo* type *hardjoprajitno*.

Methods of the invention, as well as uses of the compositions of the invention, include, but are not limited to, a method of or use for provoking an immune response against a *Lep-* tospira borgpetersenii serovar *hardjo* type *hardjo-bovis* infection in a subject comprising the step of administering to the subject an immunogenic composition comprising one or more *Leptospira interrogans* serovar *hardjo* type *hardjoprajitno* bacterium or bacteria as defined herein. Preferably, the immune response is provoked against more than one serotype or strain of *Leptospira borgpetersenii* serovar *hardjo* type *hardjo-bovis*. Compositions of the invention may be used to treat or alternatively to prevent a *Leptospira borgpetersenii* serovar *hardjo* (type *hardjo-bovis*) infection. Preferably, such immune response reduces the incidence of or severity of one or more clinical signs associated with or caused by the infection with one or more *Leptospira borgpetersenii* serovar *hardjo* type *hardjo-bovis* serotypes.

Herein, suitable subjects and subjects in need to which compositions of the invention may be administered include animals and humans in need of either prophylactic or treatment for a viral, microbial, parasitic, protozoan, bacterial, or fungal associated infection, disease, or condition. Animals in which the immune response is stimulated by use of compositions or methods of the invention include livestock, such as swine, bovines, poultry (e.g. chickens, ducks, geese, or turkeys), goats, and sheep, and domestic animals, such as mice, rabbits, dogs, cats, and horses. Preferred animals include bovines, most preferably cows and heifers.

The invention also provides a method, as well as a use of the compositions of the invention, of reducing the incidence of or severity of one or more clinical signs associated with or caused by *Leptospira borgpetersenii* serovar *hardjo* type *hardjo-bovis* infection, comprising the step of administering an immunogenic composition of the invention that comprises one or more *Leptospira interrogans* serovar *hardjo* type *hardjoprajitno* bacterium or bacteria as provided herewith and preferably a carrier molecule, such that the incidence of or the severity of a clinical sign of the *Leptospira borgpetersenii* serovar *hardjo* type *hardjo-bovis* infection is reduced by at least 10%, preferably by at least 20%, even more preferably by at least 30%, even more preferably by at least 50%, still more preferably by at least 70%, and most preferably by 100% relative to a subject that has not received the immunogenic composition as provided herewith.

According to a further aspect, the present invention also relates to a method, as well as a use of the compositions of the invention, for the prophylaxis of a *Leptospira borgpetersenii* serovar *hardjo* type *hardjo-bovis* infection comprising the step of administering an immunogenic composition of the invention that comprises one or more *Leptospira interrogans* serovar *hardjo* type *hardjoprajitno* as provided herewith.

Another aspect of the invention provides a method of producing one or more *Leptospira interrogans* serovar *hardjo* type *hardjoprajitno* bacterium or bacteria that induce an immune response against at least one serotype of *Leptospira borgpetersenii* serovar *hardjo* type *hardjo-bovis*), and more preferably two or more serotypes of *Leptospira borgpetersenii* serovar *hardjo* (type *hardjo-bovis*. This method comprises culturing a transformed expression vector coding for and expressing one or more of the *Leptospira interrogans* serovar *hardjo* (type *hardjoprajitno*) bacterium or bacteria disclosed herein. The expressed bacterium or bacteria are either retained by the expression organism or secreted into the culture medium. Expression is conducted under conditions sufficient to produce *Leptospira interrogans* serovar *hardjo* type *hardjoprajitno* bacteria capable of inducing an immune response to *Leptospira borgpetersenii* serovar *hardjo* type *hardjo-bovis*.

Methods of making compositions of the invention may further comprise admixing one or more *Leptospira interrogans* serovar *hardjo* type *hardjoprajitno* bacterium or bacteria and a carrier molecule with a physiologically-acceptable vehicle such as a pharmaceutically- or veterinary-acceptable carrier, adjuvant, or combination thereof. Those of skill in the art will recognize that the choice of vehicle, adjuvant, or combination will be determined by the delivery route, personal preference, and animal species among others.

In another aspect, the invention provides a method, as well as a use of the compositions of the invention, of diagnosing a *Leptospira borgpetersenii* serovar *hardjo* (type *hardjo-bovis*) infection in a subject. The method and use comprise providing one or more *Leptospira interrogans* serovar *hardjo* type *hardjoprajitno* bacterium or bacteria; contacting the one or more *Leptospira interrogans* serovar *hardjo* type *hardjoprajitno* bacterium or bacteria with a sample obtained from the subject; and identifying the subject as having a *Leptospira borgpetersenii* serovar *hardjo* type *hardjo-bovis* infection if an antibody capable of binding the one or more *Leptospira interrogans* serovar *hardjo* type *hardjoprajitno* bacterium or bacteria is detected in the sample.

The invention also provides kits that comprise an immunogenic composition that comprises one or more *Leptospira interrogans* serovar *hardjo* type *hardjoprajitno* bacterium or bacteria, optionally together with a carrier molecule; a container for packaging the immunogenic composition; a set of printed instructions; and a dispenser capable of administering the immunogenic composition to an animal. Optionally, the one or more *Leptospira interrogans* serovar *hardjo* type *hardjoprajitno* bacterium or bacteria and the carrier molecule may be packaged as together or as separate compounds. When supplied separately, a means of admixing or conjugating the one or more *Leptospira interrogans* serovar *hardjo* type *hardjoprajitno* bacterium or bacteria and carrier molecule, as well as appropriate printed instructions, is also supplied.

The invention also provides kits for vaccinating an animal comprising a set of printed instructions; a dispenser capable of administering the immunogenic composition provided herewith comprising one or more *Leptospira interrogans* serovar *hardjo* type *hardjoprajitno* bacterium or bacteria to an animal; and wherein at least one of *Leptospira interrogans* serovar *hardjo* type *hardjoprajitno* bacterium or bacteria effectively immunizes the animal against at least one disease associated with *Leptospira borgpetersenii* serovar *hardjo* type *hardjo-bovis* infection. Preferably, the one or more *Leptospira interrogans* serovar *hardjo* type *hardjoprajitno* bacterium or bacteria are selected from those provided herewith. Kits of the invention may further comprise a veterinary acceptable carrier, adjuvant, or combination thereof.

The dispenser in a kit of the invention is capable of dispensing its contents as droplets; and the immunogenic composition comprises the *Leptospira interrogans* serovar *hardjo* type *hardjoprajitno* bacterium or bacteria as provided herewith included in the kit is capable of reducing the severity of at least one clinical sign of a *Leptospira borgpetersenii* serovar *hardjo* type *hardjo-bovis* infection when administered subcutaneously, intranasally, intradermally, or intramuscularly to an animal. Preferably, the severity of a clinical sign is reduced by at least 10% preferably by at least 20%, even more preferably by at least 30%, even more preferably by at least 50%, still more preferably by at least 70%, and most preferably by 100% as compared to an untreated, infected animal.

Methods and uses of compositions of the invention for the treatment or prophylaxis of infections caused by *Leptospira borgpetersenii* serovar *hardjo* type *hardjo-bovis* are also disclosed. The methods and uses comprise administering an effective amount of a *Leptospira interrogans* serovar *hardjo* type *hardjoprajitno* bacterium or bacteria to a subject, wherein said treatment or prophylaxis is selected from the group consisting of reducing signs of *Leptospira borgpetersenii* serovar *hardjo* type *hardjo-bovis* infection, reducing the severity of or incidence of clinical signs of *Leptospira borgpetersenii* serovar *hardjo* type *hardjo-bovis* infection, reducing the mortality of subjects from *Leptospira borgpetersenii* serovar *hardjo* type *hardjo-bovis* infection, and combinations thereof.

Compositions of the invention further comprise a veterinarily acceptable carrier, adjuvant, or combination thereof. Such compositions may be used as a vaccine and comprise an attenuated vaccine, an inactivated vaccine, or combinations thereof. Such vaccines elicit a protective immunological response against at least one disease or clinical symptom associated with a *Leptospira borgpetersenii* serovar *hardjo* type *hardjo-bovis* infection.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods and uses of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

The invention also provides a method or use of the invention for reducing the severity of a *Leptospira borgpetersenii* serovar *hardjo* type *hardjo-bovis* infection in an animal comprising administering to the animal a composition that comprises a *Leptospira interrogans* serovar *hardjo* type *hardjoprajitno* bacterium or bacteria.

Methods, as well as uses of the compositions of the invention, for the treatment or prophylaxis of infections caused by *Leptospira borgpetersenii* serovar *hardjo* type *hardjo-bovis* are also disclosed. The method comprises administering an effective amount of the *Leptospira interrogans* serovar *hardjo* type *hardjoprajitno* bacterium or bacteria of the present invention to an animal.

Preferred routes of administration include subcutaneous, intranasal, intradermal, and intramuscular. The skilled artisan will recognize that compositions of the invention may also be administered in two or more doses, as well as, by other routes of administration. For example, such other routes include subcutaneously, intracutaneously, intravenously, intravascularly, intraarterially, intraperitnoeally, intrathecally, intratracheally, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating an animal comprising a set of printed instructions; a dispenser capable of administering a vaccine to an animal; and at least one killed *Leptospira interrogans* serovar *hardjo* type *hardjoprajitno* bacterium or bacteria that effectively immunizes the animal against at least one disease associated with *Leptospira borgpetersenii* serovar *hardjo* type *hardjo-bovis*. Kits of the invention may further comprise a veterinarily acceptable carrier, adjuvant, or combination thereof.

The dispenser in a kit of the invention is capable of dispensing its contents as droplets; and the isolate included in the kit is capable of reducing the severity of at least one clinical sign of a *Leptospira borgpetersenii* serovar *hardjo* type *hardjo-bovis* infection when administered intranasally, orally, intradermally, or intramuscularly to an animal. In some kits, the isolate is also capable of reducing the severity of at least one clinical sign of a *Leptospira borgpetersenii* serovar *hardjo* type *hardjo-bovis* infection. Preferably, the severity of a clinical sign is reduced by at least 10% as compared to an untreated, infected animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The present invention provides immunogenic compositions, vaccines, and related methods and uses that provide protection against, reduce the incidence, and/or lessen the severity of infection by *Leptospira borgpetersenii* serovar *hardjo* type *hardjo-bovis* by vaccinating with *Leptospira interrogans* serovar *hardjo* type *hardjoprajitno*.

The present invention demonstrates the ability of the LHP component of two different combination vaccines to protect against challenge with LHB. Post-challenge culture results showed that none of the vaccinated heifers in either vaccine treatment group (Groups 1 and 2, Example 1) had infection as a result of challenge (see Tables 2 and 6, Example 1). These results were in sharp contrast to the placebo control vaccinated animals where 100% of the heifers became infected (see Tables 2, 3 and 5, Example 1).

In contrast to the results reported here, previous studies have reported that vaccines containing LHP have not shown good protection against urine shedding or renal infection when vaccinated animals are challenged with LHB. Subtle differences in the serovar of *hardjo* used to prepare the vaccine may, in part, account for the level of protection provided by this vaccine. Such distinctions may include differences in the original isolate, as well as, differences induced based on methods of growth and passage.

It is understood in the art that the level of protection provided by a vaccine will depend not only on the specifics of the serovar/strain of the organism contained in the vaccine, but also on the adjuvant, if any, used in the formulation of the vaccine. Here, the vaccines used included an adjuvant(s). Further, growth and inactivation conditions utilized for production of the strain can also impact the efficacy provided by the vaccine. Serovar differences combined with adjuvant formulation and organism processing for the vaccine can affect the ability of the vaccine to induce a protective immune response. Any or all of these factors combined may account for the prior failures of others and the success of the present invention.

Vaccination with both the modified live viral/LHP bacterin combination and killed viral/LHP bacterin combination resulted in prevention of urine shedding as well as prevention of renal infection and colonization after challenge with LHB. The results of this study show that the *L. hardjo* component of the test vaccines is highly efficacious against challenge induced renal infection and colonization and associated urinary shedding due to LHB.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular bacterial cultures or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "a vaccine" includes a mixture of two or more antigens, reference to "an immunogenic composition" includes mixtures of two or more immunogenic vaccine components, and the like.

A. Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection is lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably a *Leptospira borgpetersenii* serovar *hardjo* type *hardjo-bovis*, respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3, 4, 5, 6, or 7 months, still more preferably 8, 9, 10, 11, or 12 months, still even more preferably 13, 14, 15, 16, 17, or 18 months, and most preferably 19 months or longer. In the case of livestock, it is most preferred that the long lasting protection shall persist until the average age at which animals are marketed for meat. In case of heifers or cows, it is most preferred that the long lasting protection shall persist until the average age at which the animals are retired from breeding and marketed.

An "immunogenic or immunological composition" refers to a composition of matter that comprises at least one *Leptospira interrogans* serovar *hardjo* (type *hardjoprajitno*), or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a *Leptospira borgpetersenii* serovar *hardjo* (type *hardjo-bovis*) infection.

An "immune response" or "immunological response" mean, but are not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of *Leptospira borgpetersenii* serovar *hardjo* type *hardjo-bovis* infection but does not react with an antigen characteristic of a strict challenge control.

As used herein, ""a pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., QUIL A®, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with allyl sucrose or with allyl pentaerythritol. Among them, there may be mentioned CARBOPOL® 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, AVRIDINE® lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in the animal against *Leptospira borgpetersenii* serovar *hardjo* type *hardjo-bovis*.

"Mortality", in the context of the present invention, refers to death caused by *Leptospira borgpetersenii* serovar *hardjo* type *hardjo-bovis* infection, and includes the situation where the infection is so severe that an animal is euthanized to prevent suffering and provide a humane ending to its life.

"Attenuation" means reducing the virulence of a pathogen. In the present invention "attenuation" is synonymous with "avirulent". In the present invention, an attenuated bacterium is one in which the virulence has been reduced so that it does not cause clinical signs of a Leptospirosis but is capable of inducing an immune response in the target mammal, but may also mean that the clinical signs are reduced in incidence or severity in animals infected with the attenuated *Leptospira interrogans* serovar *hardjo* type *hardjoprajitno* in comparison with a "control group" of animals infected with non-attenuated *Leptospira interrogans* serovar *hardjo* type *hardjoprajitno* and not receiving the attenuated bacterium. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent *Leptospira interrogans* serovar *hardjo* type *hardjoprajitno* strain is one that is suitable for incorporation into an immunogenic composition comprising a modified live *Leptospira interrogans* serovar *hardjo* type *hardjoprajitno* bacterium.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "immunoreactive to *Leptospira borgpetersenii* serovar *hardjo* (type *hardjo-bovis*)" as used herein means that the peptide or fragment elicits the immunological response against *Leptospira borgpetersenii* serovar *hardjo* type *hardjo-bovis*.

B. Adjuvants

In order to further increase the immunogenicity of the immunogenic compositions provided herewith, and which contain one or more *Leptospira interrogans* serovar *hardjo* type *hardjoprajitno* may also comprise one or more adjuvants.

The adjuvant may be purified by any of the techniques described previously or known in the art. The preferred purification technique is silica gel chromatography, in particular the "flash" (rapid) chromatographic technique, as described by W. Clark Still et al, J. Organic Chemistry, 43, 2923-2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the *Leptospira interrogans* serovar *hardjo* type *hardjoprajitno* under appropriate sterile conditions in accordance with known techniques to produce the adjuvanted composition. Complexation of the *Leptospira interrogans* serovar *hardjo* type *hardjoprajitno* and the adjuvant is facilitated by the existence of a net negative charge on the conjugate which is electrostatically attracted to the positive charge present on the long chain alkyl compound adjuvant.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01% to 75%, preferably at a concentration of about 2% to 30%, more preferably at a concentration of about 5% to 25%, still more preferably at a concentration of about 7% to 22%, and most preferably at a concentration of 10% to 20% by volume of the final product.

C. Physiologically-Acceptable Vehicles

The vaccine compositions of this invention may be formulated using techniques similar to those used for other pharmaceutical polypeptide compositions. Thus, the adjuvant and *Leptospira interrogans* serovar *hardjo* type *hardjoprajitno* may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that improved immunological effectiveness of the immunogenic composition is appropriate.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably between about 0.2 ml and about 0.5 ml at the concentrations of conjugate and adjuvant noted above.

The vaccine compositions of the invention may be administered by any convenient, suitable means.

D. Formulation

Immunogenic compositions comprising *Leptospira interrogans* serovar *hardjo* type *hardjoprajitno* can be used as vaccines for immunization against *Leptospira borgpetersenii* serovar *hardjo* type *hardjo-bovis*. The vaccines, comprising the immunogenic composition in a physiologically acceptable vehicle, are useful in a method of immunizing animals, preferably cattle, preferably cows, most preferably heifers, for treatment or prevention of infections by *Leptospira borgpetersenii* serovar *hardjo* type *hardjo-bovis*.

Antibodies generated against immunogenic compositions of the present invention by immunization with an immunogenic composition can be used in passive immunotherapy and generation of antiidiotypic antibodies for treating or preventing infections of *Leptospira borgpetersenii* serovar *hardjo* type *hardjo-bovis*.

The subject to which the composition is administered is preferably an animal, including but not limited to cows, horses, sheep, pigs, poultry (e.g., chickens), goats, cats, dogs, hamsters, mice and rats, most preferably the animal is a cow or heifer.

The formulations of the invention comprise an effective immunizing amount of one or more immunogenic compositions or antibodies thereto and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

E. Effective Dose

The compounds described herein can be administered to a subject at therapeutically effective doses to treat Leptospirosis-associated diseases. The dosage will depend upon the host receiving the vaccine as well as factors such as the size, weight, and age of the host.

The precise amount of immunogenic conjugate or antibody of the invention to be employed in a formulation will depend on the route of administration and the nature of the subject (e.g., species, age, size, stage/level of disease), and should be decided according to the judgment of the practitioner and each subject's circumstances according to standard clinical techniques. An effective immunizing amount is that amount sufficient to treat or prevent a *Leptospira borgpetersenii* serovar *hardjo* type *hardjo-bovis* infectious disease in a subject. Effective doses may also be extrapolated from dose-response curves derived from animal model test systems and can vary from 0.001 mg/kg to 100 mg/kg.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in animals, especially cattle. The dosage of such compounds lies preferably within a range of circulating concentrations that include the $ED_{50}$ with little or no toxicity. The dosage can vary within this range depending upon the dosage form employed and the route of administration utilized. For any compound used in the methods of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

Immunogenicity of a composition can be determined by monitoring the immune response of test subjects following immunization with the composition by use of any immunoassay known in the art. Generation of a humoral (antibody) response and/or cell-mediated immunity, may be taken as an indication of an immune response. Test subjects may include animals such as pigs, mice, hamsters, dogs, cats, rabbits, cows, horses, sheep, poultry (e.g. chickens, ducks, geese, and turkeys), and humans.

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals or humans. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal with a *Leptospira interrogans* serovar *hardjo* type *hardjoprajitno* using the methods and compositions of the present invention, any binding assay known in the art can be used to assess the binding between the resulting antibody and the particular molecule. These assays may also be performed to select antibodies that exhibit a higher affinity or specificity for the particular antigen.

F. Detection and Diagnostic Methods

Antibodies, or binding portions thereof, resulting from the use of *Leptospira interrogans* serovar *hardjo* type *hardjoprajitno* compositions of the present invention are useful for detecting in a sample the presence of *Leptospira*. This detection method comprises the steps of providing an isolated antibody or binding portion thereof raised against an *Leptospira interrogans* serovar *hardjo* type *hardjoprajitno* of the invention, adding to the isolated antibody or binding portion thereof a sample suspected of containing a quantity of *Leptospira*, and detecting the presence of a complex comprising the isolated antibody or binding portion thereof bound to *Leptospira*.

The antibodies or binding portions thereof resulting from the use of *Leptospira interrogans* serovar *hardjo* type *hardjoprajitno* compositions of the present invention are also useful for detecting in a sample the presence of a *Leptospira*. This detection method comprises the steps of providing an isolated antibody or binding portion thereof raised against a *Leptospira interrogans* serovar *hardjo* type *hardjoprajitno*, adding to the isolated antibody or binding portion thereof a sample suspected of containing a quantity of *Leptospira*, and detecting the presence of a complex comprising the isolated antibody or binding portion thereof bound to the *Leptospira*.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody resulting from the use of *Leptospira interrogans* serovar *hardjo* type *hardjoprajitno* compositions of the present invention that immunospecifically binds to a *Leptospira* may be used to diagnose, prognose or screen for a *Leptospira* infection.

In another aspect, the invention provides a method of diagnosing or screening for the presence of a *Leptospira* infection or immunity thereto, comprising measuring in a subject the level of immunospecific binding of an antibody to a sample derived from the subject, in which the antibody immunospecifically binds a *Leptospira* peptide in which an increase in the level of said immunospecific binding, relative to the level of said immunospecific binding in an analogous sample from a subject not having the infectious disease agent, indicates the presence of *S. suis*.

Examples of suitable assays to detect the presence of *Leptospira* peptides or antagonists thereof include but are not limited to ELISA, radioimmunoassay, gel-diffusion precipitation reaction assay, immunodiffusion assay, agglutination assay, fluorescent immunoassay, Protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The binding activity of a given antibody may be determined according to well-known methods. Those skilled in the art will be able to determine operative and optimal assay conditions for each determination by employing routine experimentation.

An additional aspect of the present invention relates to diagnostic kits for the detection or measurement of LHB. Kits for diagnostic use are provided, that comprise in one or more containers an anti-*Leptospira interrogans* serovar *hardjo* type *hardjoprajitno* antibody, and, optionally, a labeled binding partner to the antibody. Alternatively, the anti-*Leptospira interrogans* serovar *hardjo* type *hardjoprajitno* antibody can be labeled (with a detectable marker, e.g., a chemiluminescent, enzymatic, fluorescent, or radioactive moiety). Accordingly, the present invention provides a diagnostic kit comprising, an anti-*Leptospira interrogans* serovar *hardjo* type *hardjoprajitno* antibody and a control immunoglobulin. In a specific embodiment, one of the foregoing compounds of the container can be detectably labeled. A kit can optionally further comprise in a container a predetermined amount of a *Leptospira interrogans* serovar *hardjo* (type *hardjoprajitno*) recognized by the antibody of the kit, for use as a standard or control.

G. Administration to a Subject

Preferred routes of administration include but are not limited to intravascular, and intramuscular. The skilled artisan will recognize that compositions of the invention may also be administered in one, two or more doses, as well as, by other routes of administration. For example, such other routes include oral, intradermal, intranasal, subcutaneous, intracutaneous, intravenous, intraarterial, intraperitnoeal, intrathecal, intratracheal, intracardial, intralobal, intramedullar, intrapulmonary, and intravaginal. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

A. Materials and Methods

Animals. All procedures involving cattle were approved by the Animal Care and Use Committee at Rural Technologies Incorporated (RTI). Ten days prior to vaccination, fifty-five (55) six-month-old Holstein heifers arrived at a dry lot housing facility. All animals were healthy, had no vaccination history to Leptospira and were serologically negative to six serovars of *Leptospira* (*pomona, hardjo, grippotyphosa, brataslava, canicola*, and *icterohemorrhagiae*) by serological Leptospira Microscopic Agglutination Test (MAT). In addition, all 55 animals were ear notch negative to Bovine Viral Diarrhea Virus (BVDV) via immunohistochemical (IHC) testing. Fifty-five animals were initially procured to ensure that a minimum of fifty (50) animals would be available for the vaccination and challenge portions of the study as well as two (2) animals for the passage of the challenge material.

Animal Housing and Feeding. Upon arrival, animals were group housed in a 33,750 square feet (sq. ft.) dry lot with a 150 feet (ft.) concrete fence-line bunk. Animals were moved as a group into a hoop barn approximately 4,080 sq. ft. in size prior to challenge. The hoop barn facility provided 100 ft. of bunk line space with head-locks, as well as two automatic waterers. All animals were fed an age appropriate grain ration with grass hay and water provided ad libitum. Additionally, feed was utilized to entice the heifers into the head-locks on the days the animals were worked.

Masking (Blinding). The investigator and/or designees performing post-challenge clinical evaluations were blinded to the individual assignments to treatment group. Laboratory personnel testing serum, urine, and tissue samples were also blinded to the treatment group assignments.

Animal Enrollment, Randomization, and Animal Observations. The assignment of animals to treatment groups prior to the initial vaccination followed a completely randomized distribution. The heifers were assigned to treatment groups using the Random Numbers Generator in the Analysis ToolPak provided by MICROSOFT® Excel. On day 0, fifty-three (53) animals were randomly assigned to one of three treatment groups (Table 1). Two heifers were randomly selected as challenge passage animals. At the end of the study, enrolled heifers were randomly assigned to one of two necropsy dates utilizing the Random Numbers Generator as previously described.

B. Treatment Groups The following viral/bacterin combination vaccines were used in the study (Table 1):

TABLE 1

Treatment Groups, Number of Animals, and Vaccine Dose Administered

| Treatment Group | Number of Animals | Treatment/Administration | Dose |
|---|---|---|---|
| 1 | 21 | Modified Live Combination Product/Subcutaneous | 2 mL |
| 2 | 21 | Killed Virus Combination Product/Subcutaneous | 5 mL |
| 3 | 11 | Placebo Controls/Subcutaneous | 2 mL |

Treatment Group 1: Vaccinates were administered a Modified Live Combination Product consisting of Bovine Rhinotracheitis-Virus Diarrhea-Parainfluenza 3-Respiratory Syncytial Virus Vaccine, Modified Live Virus, *Campylobacter* Fetus-*Leptospira Canicola-Grippotyphosa-Hardjo-Icterohaemorrhagiae-Pomona* Bacterin (a licensed commercially available combination product, EXPRESS FP® 5 VL5, Boehringer Ingelheim Vetmedica, Inc., St. Joseph, Mo.).

Treatment Group 2: Vaccinates were administered a Killed Virus Combination Product consisting of Bovine Rhinotracheitis-Virus Diarrhea-Parainfluenza 3-Respiratory Syncytial Virus Vaccine, Killed Virus, *Campylobacter* Fetus-*Haemophilus Somnus-Leptospira Canicola-Grippotyphosa-Hardjo-Icterohaemorrhagiae-Pomona* Bacterin (an unlicensed experimental combination product, Boehringer Ingelheim Vetmedica, Inc., St. Joseph, Mo.).

Treatment Group 3: The placebo vaccinated control group was administered a modified live virus consisting of Bovine Rhinotracheitis-Virus Diarrhea-Parainfluenza 3-Respiratory Syncytial Virus Vaccine (a licensed commercially available combination product, Express FP® 5, Boehringer Ingelheim Vetmedica, Inc., St. Joseph, Mo.).

The products used for vaccination of Treatment Groups 1 and 3 were fully released commercially available products. The product used for vaccination of Group 2 was an experimental serial of product prepared specifically for use in this study. All vaccinations were administered via the subcutaneous (SC) route. The test vaccines and placebo were administered as two doses, each 2 or 5 mL as indicated in Table 1, with a 21-day interval between the vaccinations. The test vaccines used were formulated to the minimum immunizing dose amount of organisms for the *L. hardjo* component. All remaining components were batched at or above the normal release dose level.

Animal Health Examination. All animals were examined by a veterinarian and considered healthy on day 0, prior to sample collection.

Vaccination. Animals in Treatment Groups 1, 2 and 3 were vaccinated on post-vaccination (PV) day 0 and 21 as outlined herein. Post-vaccination adverse effects were not seen in any of the animals.

Blood Sample Collection. Blood samples were collected from all animals on PV days 0, 21, 35, 43, 105, 112, 119, 126, 133, 140, 147, 154 and 160 via jugular venipuncture. Tubes were labeled with the date and the animals' identification (ID) number and returned to the laboratory for processing. The samples were allowed to clot at room temperature, centrifuged at 800×g for 15 minutes, then aliquoted.

Microagglutination Test (MAT). Serum samples were processed as described above and an aliquot was submitted to South Dakota State University Animal Disease Research and Diagnostic Laboratory (SDSU ADRDL) for *leptospira* MAT testing to determine antibody response to *Leptospira canicola, grippotyphosa, hardjo, icterohaemorrhagiae, bratislava* and *pomona*. The test was performed by adding known live cultures of *Leptospira* to equal amounts of diluted serum and observing the mixture microscopically for agglutination at the end of the reaction time. The end-point titer was the highest serum dilution showing agglutination of at least 50% of the leptospires in the test well. Based on the SDSU ADRDL MAT procedure, a MAT endpoint titer >100 was considered to be positive. Strain LHP was used in the *L. hardjo* MAT.

Urine Collection. Two 50-mL conical vials of urine were taken from each heifer on PV days 0, 105, 112, 119, 126, 133, 140, 147, 154, and 160. Samples were collected during midstream urination. The samples were obtained after administering 500 mg furosemide (Furosemide, Vedco Inc., St. Joseph, Mo.) intravenously (IV) to each heifer. Following collection, the outside of each vial was disinfected, labeled with animals' ID numbers, and transported to the RTI laboratory for processing for *Leptospira* culture.

Urine Cultures. The urine samples were used to detect Leptospires in the urine via culturing. Briefly, 1 mL of urine from each heifer was serially diluted 1:10 in transport medium to the $10^{-2}$ dilution. Sample volumes of 100 and 300 µL from each dilution were inoculated in Ellis (80/40) culture medium and incubated at 29° C. for up to two months. Cultures were observed microscopically for signs of *Leptospira* growth. Culture samples showing positive growth were confirmed to be *Leptospira* by dark-field microscopy. Cultures showing no growth after 2 months of observation were considered to be negative.

Kidney Cultures. Immediately following euthanasia, both kidneys were removed from each heifer. Tissue samples totaling approximately 1 cm²/1 gram of tissue per each kidney were collected. If suspect areas of the kidney were noted, characterized by pale areas of depression on the surface of the kidney, tissue samples were obtained from those areas. If no suspect areas were seen, samples were taken at random from each kidney. Each kidney sample was homogenized, and the kidney homogenates were diluted in growth medium and incubated at 29° C. for up to two months. Cultures were observed microscopically for signs of *leptospira* growth. Culture samples showing positive growth were confirmed to be *leptospira* by dark-field microscopy. Cultures showing no growth after 2 months of observation were considered to be negative.

C. Production of Challenge Phase

Animals. On PV study day 25, the two untreated heifers (#'s 29 and 48) used for production of challenge inoculum were moved to a separate building at the same facility for challenge. The animals were maintained on the same ration as the remaining groups, and allowed free access to grass hay. Water was provided ad libitum.

Challenge Material. The LHB strain 203 used for the challenge was originally obtained from the National Animal Disease Center, Ames, Iowa. This strain has been previously described. See Bolin, et. al., 1989(a); Bolin et al., 1989(b); and Bolin et al., 1991.

Challenge Preparation. The two passage heifers were challenged on PV study days 25, 26, and 27. Each heifer was challenged intraocularly with approximately $1.4 \times 10^7$ freshly grown LHB culture contained in 1.0 ml inoculum on each challenge day. The animals were restrained in a chute and the head secured with a halter. Animals were challenged intraocularly by pulling the lower eyelid down to expose the conjunctival sac. A volume of 0.5 mL of challenge material was dropped into each sac, one eye at a time, and each eyelid was held closed for 60 seconds following administration of the challenge material.

Blood and urine samples were obtained from the two passage heifers on post-first challenge days 0, 15, 23, 28, 36, 42 and 51 to follow progress of the infection. Urine samples collected from both animals were tested for presence of the organism. The culture on Heifer #48 was positive for leptospire in the urine beginning the third week following challenge and continuing until necropsy. The urine cultures on Heifer #29 were positive for leptospire on the sixth and seventh week following challenge.

On day 51 post-first challenge, animals #29 and #48 were humanely euthanized by IV administration of a barbiturate (Euthanasia 6 Grain, Vedco Inc., St. Joseph, Mo.) overdose.

The kidneys were removed from the animals and transported to the RTI laboratory for processing and *leptospira* isolation. Suspect lesions from each kidney of Heifer #48 were removed, weighed, and homogenized before adding to the culture media. No suspect lesions were found on the kidneys from Heifer #29 thus random sections were removed, weighed, and homogenized before adding to the culture media. The kidney homogenates were diluted in growth medium and cultured. Kidney cultures were grown under the same conditions as the urine, as described herein.

The kidney samples taken at the time of necropsy from Heifer #48 were culture positive, while those from Heifer #29 were negative. The positive kidney cultures were passaged into fresh growth medium to produce the challenge inoculum. The challenge inoculum was checked weekly to determine organism growth and motility. The challenge inoculum was considered ready when motility was high and sufficient culture was available for three challenges of all study animals with 1 ml inoculum containing approximately $10^6$ organisms per mL. The identities of the cultures as Leptospira were confirmed by darkfield microscopy.

Example 1

Efficacy of Vaccination and Challenge in Heifers

The purpose of this study was to evaluate efficacy of the LHP component of a commercial pentavalent combination vaccine against a virulent challenge with LHB. Efficacy was based on 1) reduction of renal infection/colonization, and 2) reduction in urinary shedding of the challenge strain. The treatments include a modified live virus (MLV) and bacterin combination vaccine (a licensed commercially available combination product, EXPRESS FP® 5 VL5, Boehringer Ingelheim Vetmedica, Inc., St. Joseph) (Group 1), a killed virus bacterin combination vaccine (an unlicensed experimental combination product, Boehringer Ingelheim Vetmedica, Inc., St. Joseph, Mo.) (Group 2), and a placebo control group vaccinated with modified live virus vaccine without the lepto bacterin (a licensed commercially available combination product, EXPRESS FP® 5, Boehringer Ingelheim Vetmedica, Inc., St. Joseph, Mo.) (Group 3).

Efficacy was determined by comparison of vaccinated and control heifers based on post-challenge organism recovery in urine and in kidney tissue at necropsy. Prevented fractions and corresponding 95% confidence limits were constructed for each variable.

A. Procedures

Vaccination. Animals in Treatment Groups 1, 2, and 3 were vaccinated on PV day 0 and 21 as outlined above. No post-vaccination adverse effects were seen in any of the animals.

Challenge. LHB strain 203 was grown in the RTI laboratory following the two-animal challenge passage phase as described above and was used for challenge. On PV days 105, 106, and 107, fresh material was counted on a hemocytometer and aliquoted into 3 mL syringes, each containing 1 mL of challenge material at approximately $10^6$ leptospires per mL. Additionally, a post-challenge sample was returned to the RTI laboratory and counted on a hemocytometer. The aliquots were used to challenge the heifers in Groups 1, 2 and 3 intraocularly as described above. Briefly, the animals were restrained and challenged intraocularly by pulling the lower eyelid down to expose the conjunctival sac. A volume of 0.5 mL of challenge material was dropped into each sac, one eye at a time. Each eyelid was held closed for 60 seconds following administration of the challenge material.

Post Challenge Observations. The animals were observed once daily for general clinical signs from the day of challenge through the day of necropsy.

Blood and Urine Sample Collection. Blood samples were collected via jugular venipuncture from all animals just prior to challenge, and weekly from 7 to 55 Days Post Challenge (DPC). The samples were processed as described above, and an aliquot was submitted to SDSU ADRDL for *Leptospira* MAT testing. Two 50 mL conical vials of urine were taken from each animal once weekly from 0 through 55 DPC. Samples were collected as described above. The urine samples were used to detect leptospires in the urine via culture as described above.

Animal Disposition and Tissue Sample Collection. On PV day 161 and 162 (56 and 57 DPC), animals (n=53) were transported to SDSU ADRDL for necropsy and tissue sample collection. Approximately half the heifers were randomly assigned to necropsy on day 161 and the second half assigned for necropsy on day 162. The animals were humanely euthanized by IV administration of a barbiturate overdose. Immediately following euthanasia both kidneys were removed from each carcass. Suspect lesions were taken from the kidneys. If no suspect lesions were observed, random samples were collected from the kidneys. The samples were weighed and homogenized prior to addition to the culture media. The tissue cultures were grown under the same conditions as the urine, as previously described.

Statistical Analysis. The 53 animals were randomly assigned to treatment groups, with 21 heifers in both Group 1 and 2, and 11 animals in Group 3 (placebo control group). Urine samples were evaluated for organism recovery on PV day 0, PV day 105 (0 DPC), PV day 112 (7 DPC), PV day 119 (14 DPC), PV day 126 (21 DPC), PV day 133 (28 DPC), PV day 140 (35 DPC), PV day 147 (42 DPC), PV day 154 (49 DPC), and PV day 160 (55 DPC). Kidney tissue samples were evaluated for organism recovery following necropsy.

Prevented fractions were used to compare organism recovery for urine shedding and kidney culture between the vaccine and control groups. Organism recovery for urine shedding was defined as the (1) presence of at least one positive urine culture during the study or (0) no positive urine cultures on any study day. Organism recovery for kidney tissue samples was defined as (1) a positive kidney culture or (0) a negative kidney culture.

The estimated prevented fraction (pf) was calculated as the complement of the risk ratio, and was defined as: $pf=1-(y_2/n_2)/(y_1/n_1)$, where $y_2$=number affected ("present" or =1) in the treated group, $n_2$=total number in the treated group, $y_1$=number affected ("present" or =1) in the control group, and $n_1$=total number in the control group.

STATXACT® 8.0 was used to compute the exact 95% confidence interval of the risk ratio based on the standardized statistic and inverting two 1-sided tests. The confidence limits for the prevented fraction are the compliment of the confidence limits for the risk ratio, or [1-U, 1-L]. The corresponding two-sided value produced by STATXACT® 8.0 was reported. The p-value for the exact test for preventive fraction=0 (Ho) is the same as the p-value for the exact test for the risk ratio=1 provided by STATXACT®. The entire 95% confidence interval is greater than 0.0% when the prevented fraction is significantly different (p<0.05) from 0.0%.

All hypothesis testing was conducted using a p-level of 0.05. Zero and near-zero values for the number of animals affected (number "present" or =1) within the groups being compared can result in unstable confidence limits and p-values.

B. Results

Microaggluntination Test Results. Blood samples were taken from all enrolled heifers in Groups 1, 2 and 3 on PV days 0, 21, 35 and 43 for MAT testing to determine antibody response to *Leptopsira canicola, grippotyphosa, hardjo, icterohaemorrhagiae* and *pomona*. Transient post-vaccination MAT serological responses were detected to the *L. canicola, grippotyphosa, icterohaemorrhagiae* and *pomona* serovars in 40 to 75 percent of the vaccinated heifers on 14 and 21 days after the second vaccination in both vaccination groups (data not shown). Transient positive MAT serological response to the *L. hardjo* were observed only on day 14 post second vaccination in less than 24 percent of the vaccinates. All unvaccinated controls remained negative to all serovars through the day of challenge.

Post-challenge blood samples were taken from all enrolled heifers in Groups 1, 2 and 3 on 0, 7, 14, 21, 28, 35, 42, 49 and 55 DPC for MAT testing to determine antibody response to *L. canicola, grippotyphosa, hardjo, icterohaemorrhagiae* and *pomona*. Post-challenge MAT antibody responses remained negative for *L. canicola, grippotyphosa, icterohaemorrhagiae* and *pomona* in all animals through the end of the study. Post-challenge MAT results for the *L. hardjo* remained negative in all vaccinated heifers from Groups 1 and 2 through the end of the study. However, in Group 3 control heifers, post-challenge MAT antibody response was evident in 9 of 11 by 14 DPC, and in 11 of 11 (100%) by 21 DPC. Peak MAT titers in the unvaccinated controls ranged from 800 (7 of 11 heifers) to 1600 (4 of 11 heifers) (data not shown).

Urine Shedding Results. All pre- and post-challenge urine cultures from all urine samples collected from the vaccinated heifers (Groups 1 and 2) were negative for growth of leptospires (Table 2). This is in contrast to placebo control heifers (Group 3) where 100% had positive urine cultures (Tables 2 and 3) with a minimum of two post-challenge samples (Table 3). The range was 2-6 positive cultures/heifer (Table 3). Urine shedding was first detected in Group 3 placebo control heifers at 21 DPC with the highest number of animals shedding at days 35 and 49 DPC (Table 3).

TABLE 2

Summarized post-challenge urine results from all heifers.

| Group | # of Heifers Positive | # of Heifers Negative | Percent Positive |
|---|---|---|---|
| 1 | 0 | 21 | 0% |
| 2 | 0 | 21 | 0% |
| 3 | 11 | 0 | 100% |

TABLE 3

Group 3 (Control) post-challenge urine culture and kidney tissue culture results.

| Heifer # | Day 0 | Day 7 | Day 14 | Day 21 | Day 28 | Day 35 | Day 42 | Day 49 | Day 55 | Kidney Culture Results |
|---|---|---|---|---|---|---|---|---|---|---|
| 4 | 0 | 0 | 0 | 1 | 1 | 1 | 1 | 1 | 0 | 0 |
| 5 | 0 | 0 | 0 | 1 | 1 | 1 | 1 | 1 | 1 | 1 |
| 6 | 0 | 0 | 0 | 1 | 1 | 1 | 1 | 1 | 1 | 1 |
| 9 | 0 | 0 | 0 | 0 | 1 | 1 | 1 | 1 | 1 | 1 |
| 23 | 0 | 0 | 0 | 0 | 1 | 1 | 0 | 1 | 1 | 1 |
| 27 | 0 | 0 | 0 | 1 | 1 | 1 | 0 | 0 | 1 | 1 |
| 28 | 0 | 0 | 0 | 1 | 1 | 1 | 1 | 1 | 0 | 1 |
| 31 | 0 | 0 | 0 | 0 | 0 | 0 | 1 | 1 | 0 | 1 |
| 34 | 0 | 0 | 0 | 1 | 0 | 1 | 1 | 1 | 1 | 1 |
| 35 | 0 | 0 | 0 | 0 | 1 | 1 | 0 | 1 | 1 | 1 |
| 52 | 0 | 0 | 0 | 0 | 1 | 1 | 1 | 1 | 0 | 1 |
| Total Positives | 0/11 | 0/11 | 0/11 | 6/11 | 9/11 | 10/11 | 8/11 | 10/11 | 7/11 | 10/11 |

0 = negative; 1 = positive

The calculated prevented fraction for urine shedding for each vaccine group compared to the placebo control was 1.0000 (100%) and the corresponding exact 95% confidence interval was [0.8389, 1.0000] or [83.9%, 100%] (Tables 4 and 5). No animals in either vaccine group had any positive urine cultures, and all animals in the control group had at least two positive urine cultures (Tables 2 and 3).

TABLE 4

Prevented Fraction and Exact 95% Confidence Limits for Presence of Organism Recovery

| Analysis Variable | Treatment Group | Prevented Fraction | Exact P-value | Lower 95% CL | Upper 95% CL |
|---|---|---|---|---|---|
| Urine | 1 vs. 3 | 1.0000 | <0.0001 | 0.8389 | 1.0000 |
|  | 2 vs. 3 | 1.0000 | <0.0001 | 0.8389 | 1.0000 |
| Kidney | 1 vs. 3 | 1.0000 | <0.0001 | 0.8349 | 1.0000 |
|  | 2 vs. 3 | 1.0000 | <0.0001 | 0.8349 | 1.0000 |

TABLE 5

Frequency and Proportion (%) Presence of Organism Recovery

| Analysis Variable | Treatment Group | Proportion Affected |
|---|---|---|
| Urine | 1 | 0/21 (0%) |
|  | 2 | 0/21 (0%) |
|  | 3 | 11/11 (100%) |
| Kidney | 1 | 0/21 (0%) |
|  | 2 | 0/21 (0%) |
|  | 3 | 10/11 (90.9%) |

Kidney Culture Results. All the vaccinated heifers (Groups 1 and 2) kidney tissues were negative for leptospire isolations (Table 6), while 10 of 11 heifers in the control group had positive leptospire cultures from kidney tissue (Tables 3 and 6).

TABLE 6

Summarized kidney culture results from Groups 1, 2 and 3.

| Group | # of Heifers Positive | # of Heifers Negative | Percent Positive |
|---|---|---|---|
| 1 | 0 | 21 | 0% |
| 2 | 0 | 21 | 0% |
| 3 | 10 | 1 | 90.9% |

The calculated prevented fraction for kidney tissue culture sample results for each vaccine groups compared to the control group was 1.0000 (100%) and the corresponding exact 95% confidence interval was [0.8349, 1.0000] or [83.5%, 100%] (Tables 4 and 5). No heifers in either vaccine group had any positive culture results (Table 6) and ten of eleven heifers in the control group had positive kidney culture results (Tables 3 and 6).

C. Conclusions

The serological MAT results show transient seroconversion post-second vaccination in a portion of the vaccinated animals for all serovars. All animals in all groups were negative by MAT for all serovars at the time of challenge (data not shown). By three weeks post-challenge, all placebo control animals were MAT positive for *L. hardjo* as a response to challenge and resulting infection with the challenge organism. Challenge of the animals with the LHB did not elicit an anamnestic MAT serological response to *L. hardjo* in the vaccinated animals, whereas 100% (11 of 11) of the placebo controls showed positive MAT results after challenge. The challenge organism was recovered utilizing culture from urine samples taken at weekly intervals through day 56 post-challenge. Each of the placebo control animals (Group 3) had a minimum of two urine samples test culture positive, indicating shedding for at least 7 days. The duration of shedding in the placebo controls ranged from 7 days to 35 days. In Group 3, one of 11 heifers shed for two sampling days; 4 of 11 shed for 4 days; 4 of 11 shed for five sampling days; and 2 of 11 shed for six sampling days. There was no organism recovery from any urine sample in any of the vaccinated animals. Based upon the culture results, vaccination with the *L. hardjo* bacterin completely prevented urine shedding of the challenge organism.

Kidney samples taken at the time of necropsy were also cultured to determine challenge organism recovery. Kidney tissues from 10 of 11 (90.9%) of the placebo controls were positive for recovery of the challenge organism. There was no recovery of the challenge organism from any kidney tissues from any of the vaccinated heifers (Groups 1 and 2). Based upon culture results, vaccination with the *L. hardjo* bacterin completely prevented kidney infection/colonization with the challenge organism.

Challenge of the heifers vaccinated with either the modified live combination product or the killed viral combination product with the LHB did not elicit an anamnestic MAT serological response to *L. hardjo*, whereas 100% (11 of 11) of the placebo controls showed positive MAT results after challenge. These results indicated that the placebo controls heifers mounted a serological MAT response as a result of the active infection. This result was in sharp contrast to the absence of a MAT serological response post-challenge in the vaccinated animals. The lack of MAT serological response in the vaccinated animals could indicate that replication of the challenge organism did not occur in these vaccinated animals, at least to an extent sufficient enough to elicit an anamnestic serological response. Others have also reported the lack of a post-challenge anamnestic serological response in *leptospira* vaccinated animals (Trueba et al., 1990; Bolin and Alt, 2001), and have discussed the possibility of a blocking effect of IgG on the epitopes of the immunogen or a negative feedback effect on B-lymphocytes receptors, therefore preventing a secondary antibody response (Trueba et al., 1990). Historically, based primarily on passive protection studies utilizing antibodies against leptospiral lipopolysaccharides in animal models, protective immunity against *L. hardjo* was thought to be antibody mediated (Jost et al., 1986; Masuzawa et al., 1990). However, studies involving challenge of animals having high titers of anti-LPS antibody at the time of challenge were not protected against challenge with *L. hardjo* (Bolin et al., 1989(b); Bolin et al., 1991). Studies conducted in cattle utilizing vaccines that provided protection against challenge with LHB strain 203 have shown that induction of a potent post-vaccination Th1 type immune response involving CD4 and $\lambda\delta$ T lymphocytes may be associated with vaccine induced protection against challenge (Naiman, et al., 2001; Naiman, et al., 2002). Perhaps the strong protective memory aspect provided by the Th1 cell mediated immune response in the vaccinated animals is able to prevent replication of the challenge organism. The result may be insufficient antigen available for recognition by the immune system of the vaccinated/challenged animal that would result in induction of an anamnestic antibody based response.

Results reported here are similar to vaccine studies that reported protection provided by a monovalent leptospiral vaccine against challenge with LHB strain 2038. The leptospiral vaccine used in those studies was reported to be prepared from LHB strain 93U, whereas the strain utilized in preparation of the vaccine for the study reported here was LHP. These are two serologically identical but genetically distinct types of serovar *hardjo* (Ellis, et al., 1986; Djordjevic, et. al., 1993; Thiermann et al., 1986; Skilbeck and Davies, 1989). In contrast to the results reported here, previous studies have reported that vaccines containing LHP have not shown good protection against urine shedding or renal infection when vaccinated animals are challenged with LHB (Bolin, et. al., 1989(a); Bolin et al., 1989(b); Bolin et al., 1991; Bolin and Alt, 2001). Subtle differences in the serovar of *hardjo* used to prepare the vaccine may, in part, account for the level of protection provided by this vaccine. Such distinctions may include differences in the original isolate, as well as, differences induced based on methods of growth and passage. The level of protection provided by a vaccine will depend not only on the specifics of the serovar/strain of the organism contained in the vaccine, but also on the adjuvant, if any, used in the formulation of the vaccine. Here, the vaccines used included an adjuvant(s). Growth and inactivation conditions utilized for production of the strain can also impact the efficacy provided by the vaccine. Serovar differences combined with adjuvant formulation and organism processing for the vaccine can affect the ability of the vaccine to induce a protective immune response.

Vaccination with both the modified live viral/LHP bacterin combination and killed viral/LHP bacterin combination resulted in prevention of urine shedding as well as prevention of renal infection and colonization after challenge with LHB. The results of this study show that the *L. hardjo* component of the test vaccines is highly efficacious against challenge induced renal infection and colonization and associated urinary shedding due to LHB.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

1. Faine S, Adler B, Bolin C A, et. al. *Leptospira* and leptospirosis, $2^{nd}$ ed. Melborne, Australia, MediSci Press, 1999.
2. Heath S and Johnson R. Leptospirosis. J Am Vet Med Assoc 205:1518-1523, 1994.
3. Ellis W A. Leptospirosis as a cause of reproductive failure. Vet Clin N Am Food Anim Pract 10-463-478, 1994.
4. Bolin, C A, Thiermann A B, et. al. Effect of vaccination with a pentavalent leptospiral vaccine on *Leptospira interrogans* serovar *hardjo* type *hardjo-bovis* infection of pregnant cattle. Am J Vet Res 50:161-165, 1989(a).
5. Bolin C A, Zuerner R L, Trueba G. Effect of vaccination with a pentavalent leptospiral vaccine containing *Leptospira interrogans* serovar *hardjo* type *hardjo-bovis* on they *hardjo-bovis* infection of cattle. Am J Vet Res. 50:2004-2008, 1989(b).
6. Bolin C A, Cassells J A, Zuerner R L, et. al. Effect of vaccination with a monovalent *Leptospira interrogans* serovar *hardjo* type *hardjo-bovis* vaccine on type *hardjo-bovis* infection of cattle. Am J Vet Res. 52:1639-1643, 1991.
7. Trueba G A., Bolin C A, Thoen C O. Evaluation of an enzyme immunoassay for diagnosis of bovine leptospirosis caused by *Leptospira interrogans* serovar *hardjo* type *hardjo-bovis*. J Vet Diagn Invest 2:323-329, 1990.
8. Bolin, C A and Alt D P. Use of a monovalent leptopsiral vaccine to prevent renal colonization and urinary shedding in cattle exposed to *Leptospria borpetersenii* serovar *hardjo*. Am J Vet Res 62(7):995-1000, 2001.
9. Jost B H, Adler B, Vihn T, Faine S. A monoclonal antibody reacting with a determinant on leptospiral lipopolysaccharide protects guinea pigs against leptospirosis. J Med Microbiol. 22:269-275, 1986.
10. Masuzawa T, Nakamura R, Hashiguchi Y, et. al. Immunological reactivity and passive protective activity of monoclonal antibodies against protective antigen (PAg) of *Leptospira interrogans* serovar *lai*. Zentbl Bakteriol Reihe A 272:328-336, 1990.
11. Naiman, B M, Alt D, Bolin C A, et. al. Protective killed *Leptospira borpetersenii* vaccine induces potent Th1 Immunity comprising responses by CD4 and $\lambda\delta$ T Lymphocytes. Infection and Immunity 69(12):7550-7558, 2001.
12. Naiman, B M, Blumerman S, Alt D, et. al. Evaluation of Type 1 immune response in naive and vaccinated animals following challenge with *Leptospira borgpetersenii* serovar *hardjo*: involvement of WC1+$\lambda\delta$ and CD4 T cells. Infection and Immunity 70(11):6147-6157, 2002.
13. Ellis, W A, Thiermann A B, Marshall R B. Genotypes of *Leptopria hardjo* and their role in clinical disease. In Proceedings. 14th World Congress Diseases of Cattle. 966-970, 1986.
14. Djordjevic S, Hornitzky M, Ross A D, et. al. Restriction endonuclease analysis of Australian isolate of *Leptospira interrogans* serovar *hardjo* from cattle with agalactia and abortion. Aust Vet J. 70(3):98-100, 1993.
15. Thiermann A B, Handaker A L, Foly J W, Kingscote B F. Reclassification of North American leptospiral isolates belonging to serogroups Mini and Sejroe by restriction endonuclease analysis. Am J Vet Res. 47:61-66, 1986.
16. Skilbeck N W and Davies W D. Restriction endonuclease analysis of Australian isolates of *Leptospira interrogans* serovar *hardjo*. Aust Vet J. 66:183-184. 1989.

What is claimed is:

1. A method of providing protection against, reduction in the incidence, and/or lessening the severity of infection by *Leptospira borgpetersenii* serovar *hardjo* type *hardjo-bovis* in a mammal comprising administering to the mammal an immunogenic composition, wherein the immunogenic composition includes a killed *Leptospira interrogans* serovar *hardjo* type *hardjoprajitno* bacterium but without including *Leptospira borgpetersenii* serovar *hardjo* type *hardjo-bovis* bacterium in said immunogenic compostion.

2. The method of claim 1, further comprising one or more modified live viruses (MLVs) selected from the group consisting of Infectious Bovine Rhinotracheitis (IBR) virus, Bovine Virus Diarrhea (BVD) Types 1 and 2, Parainfluenza 3 (PI3) virus, and Bovine Respiratory Syncytial Virus (BRSV).

3. The method of claim 1, wherein the method provokes an immune response that provides protection against, reduction in the incidence, and/or lessens the severity of the infection by *Leptospira borgpetersenii* serovar *hardjo* type *hardjo-bovis* in said mammal.

4. The method of claim 3, wherein the mammal is a bovine.

5. The method of claim 3, wherein the bovine is a cow or a heifer.

* * * * *